United States Patent [19]
Keene

[11] Patent Number: 5,972,620
[45] Date of Patent: Oct. 26, 1999

[54] METHOD OF ISOLATING RIBOTOPES AND PROTEOTOPES

[76] Inventor: Jack D. Keene, 6300 Garrett Rd., Durham, N.C. 27707

[21] Appl. No.: 09/258,658

[22] Filed: Feb. 26, 1999

Related U.S. Application Data

[62] Division of application No. 08/818,711, Mar. 14, 1997, Pat. No. 5,882,866
[60] Provisional application No. 60/013,507, Mar. 15, 1996.
[51] Int. Cl.$^6$ .......................... C12Q 1/68; G01N 33/53; C12N 15/11
[52] U.S. Cl. .............................. 435/6; 435/7.1; 536/23.1
[58] Field of Search ..................... 435/6, 7.1; 536/23.1

[56] References Cited

U.S. PATENT DOCUMENTS

| | | | |
|---|---|---|---|
| 5,270,163 | 12/1993 | Gold et al. | 435/6 |
| 5,525,495 | 6/1996 | Keene et al. | 435/172.3 |

OTHER PUBLICATIONS

Tsai and Keene; In Vitro Selection of RNA Epitopes Using Autoimmune Patient Serum; *The Journal of Immunology;* 150:1137–1145; (Feb. 1, 1993).
Keene; RNAs Selected to RRM Proteins; *Methods in Enzymology;* 267:381–383, (May 17, 1996).
Edgington; Shape Space; *Bio/Technology;* 11:285–289, (Mar. 1993).
Deutscher and Keene; A sequence–specific conformational epitope on U1 RNA is recognized by a unique autoantibody; *Proc. Natl. Acad. Sci. USA;* 85:3299–3303, (May 1988).
Bock et al.; Selection of single–stranded DNA molecules that bind and inhibit human thrombin; *Nature;* 355:564–566, (Feb. 1992).
Doudna et al.; Selection of an RNA molecule that mimics a major autoantigenic epitope of human insulin receptor; *Proc. Natl. Acad. Sci., USA;* 92:2355–2359, (Mar. 1995).
Reichlin et al.; Lupus Autoantibodies to Native DNA Cross–React with the A and D SnRNP Polypeptides; *J. Clin. Invest.;* 93:443–449, (Jan. 1994).
Gao et al.; Selection of a subset of mRNAs from combinatorial 3' untranslated region libraries using neuronal RNA–binding protein Hel–N1; *Proc. Natl. Acad. Sci. USA;* 91:11207–11211, (Nov. 1994).
Tuerk and Gold; Systematic Evolution of Ligands by Exponential Enrichment: RNA Ligands to Bacteriophage T4 DNA Polymerase; *Science;* 249:505–510, (Aug. 3, 1990).
Tsai et al.; In vitro selection of an RNA epitope immunologically cross–reactive with a peptide; *Proc. Natl. Acad. Sci. USA;* 89:8864–8868, (Oct. 1992).
Gold et al.; From oligonucleotide shapes to genomic SELEX: Novel biological regulatory loops, *Proc. Natl. Acad. Sci. USA*, vol. 94:59–64 (Jan. 1997).

*Primary Examiner*—John S. Brusca
*Attorney, Agent, or Firm*—Myers Bigel Sibley & Sajovec, P.A.

[57] ABSTRACT

Methods of making nucleic acids that inhibit complex formation between antigen binding proteins and non-nucleic acid immunogens are provided. Methods of making non-nucleic acid immunogens that inhibit complex formation between antigen binding proteins and nucleic acids are also provided herein.

10 Claims, 1 Drawing Sheet

METHOD OF ISOLATING RIBOTOPES AND PROTEOTOPES

RELATED APPLICATIONS

This application is a divisional of U.S. application Ser. No. 08/818,711, filed Mar. 14, 1997, U.S. Pat. No. 5,882,866, which application claimed the benefit of U.S. Provisional Application Serial No. 60/013,507, filed Mar. 15, 1996.

FEDERALLY SUPPORTED RESEARCH

This invention was made with government support under grant number CA60083 from the National Cancer Institute. The government has certain rights to this invention.

FIELD OF THE INVENTION

This invention relates to nucleic acids that inhibit complex formation between non-nucleic acid molecules, and methods of making the same.

BACKGROUND OF THE INVENTION

Conformational RNA epitopes were discovered because autoantibodies in the sera of patients with systemic autoimmune diseases are directly reactive with discrete structural elements in U1 snRNA, transfer RNA and ribosomal RNA. See Wilusz, J. & Keene, J. D. (1986) *J. Biol. Chem.* 261, 5467–5472; Deutscher, S. L. & Keene, J. D. (1988) *Proc. Natl. Acad. Sci. USA* 85, 3299–3303; Uchiumi, T. et al. (1991) *J. Biol. Chem.* 266, 2054–2062. These and other studies indicated that autoantibodies recognize and bind with high specificity to unique and restricted regions of cellular RNA molecules in a manner much like their binding to epitopes on proteins.

Immune reactivity with specific regions of RNA molecules was unexpected since nucleic acids are poorly immunogenic and the net negative charge on the surfaces of antibodies disfavor interactions with negatively charged phosphate backbones of RNA and DNA. Historically, the reactivity of RNA with antibodies has been viewed with skepticism as an epiphenomenon resulting from accidental crossreactivity of RNAs (now termed aptamers) with other cellular immunogens or to result from an unexplainable presentation of RNA fragments to the immune system following a breakdown in discrimination of self from non-self. However, it has been shown that unique RNA molecules can be selected in vitro from combinatorial RNA libraries to bind to antibody binding sites, indicating that conformational RNA epitopes may result from crossreactivity between RNAs and proteins that is discrete, specific, and non-coincidental. See, e.g., Tsai, D. S., et al. (1992) *Proc. Natl. Acad. Sci. USA* 89, 8864–8868; Tsai, D. S. & Keene, J. D. (1993) *J. Immunol.* 150, 1137–1145; Kenan, D. J., et al. (1994) *TIBS* 19, 57–64; Doudna, J. A., et al. (1995) *Proc. Natl. Acad. Sci. USA* 92, 2355–2359.

J. Keene et al., PCT Application No. PCT/US93/08210, describes methods of making epitopes and nucleic acids embodying the epitopes so made. Specifically, a method is described wherein an antibody can be employed to derive a nonproteinaceous mimetic ligand that binds to the same site on the antibody to which the original antigen bound. The method involves combining an antigen binding protein (e.g., an antibody, a T cell receptor) which binds the immunogen with a degenerate pool of nucleic acid species, and then recovering a nucleic acid species bound by said binding protein from the degenerate pool.

It would be highly desirable to have a means for making a nucleic acid that is immunologically cross-reactive with other molecules without the need to resort to a degenerate pool of nucleic acids.

It would also be highly desirable to have a means for making a non-nucleic acid molecule that is immunologically cross-reactive with a nucleic acid, when an antigen binding protein that specifically binds that nucleic acid is known.

SUMMARY OF THE INVENTION

The present invention is based upon the unexpected discovery that RNA conformers, called ribotopes, can compete in vivo for binding sites on cellular targets to which peptide epitopes can also bind. Therefore, the inventors have realized that ribotopes and epitopes are functional mimetics of each other, and either may elicit a conformational change or functional effect on a common target molecule.

Accordingly, a first aspect of the present invention is a method of making or isolating a nucleic acid molecule which is immunologically cross-reactive with an immunogen, which immunogen is not a nucleic acid (e.g., a peptide). The method comprises providing an antigen binding protein (e.g., an antibody, a T-cell receptor) that specifically binds to an immunogen, providing a mixture of nucleic acids obtained from a cell or virus that expresses the immunogen, and contacting the mixture to the antigen binding protein so that the nucleic acid is bound thereto. After the contacting step, the nucleic acid mixture is separated from the antigen binding protein, following which the specific nucleic acid is separated from the antigen binding protein.

A second aspect of the present invention is a method of making or isolating an immunogen that inhibits complex formation between an antigen binding protein and a nucleic acid. This method comprises the steps of providing an antigen binding protein that specifically binds a nucleic acid, providing a mixture of immunogens obtained from a cell or virus that expresses the immunogen, contacting the mixture to the antigen binding protein so that the immunogen is bound thereto, separating the mixture from the antigen binding protein, and then separating the immunogen from the antigen binding protein.

A third aspect of the present invention is an isolated nucleic acid which inhibits complex formation between an antigen binding protein and an immunogen, which immunogen is not a nucleic acid.

Heretofore, it has not been possible to derive a nucleic acid epitope that competes for a binding site with a non-nucleic acid immunogen from a pool of nucleic acids obtained from a cell or virus that expresses that immunogen.

Additionally, it has heretofore not been possible using any known method to identify RNA epitopes or ribotopes in messenger RNA, which differs from other RNA species in that it is both inabundant and generally unstable. Previous methods have identified RNA epitopes present in only abundant and stable cellular RNAs such as ribosomal RNA, transfer RNA and uridylate-rich small nuclear RNAs.

The foregoing and other objects and aspects of the present invention are explained in detail in the drawings herein and the specification set forth below.

DETAILED DESCRIPTION OF THE INVENTION

Figure 2:
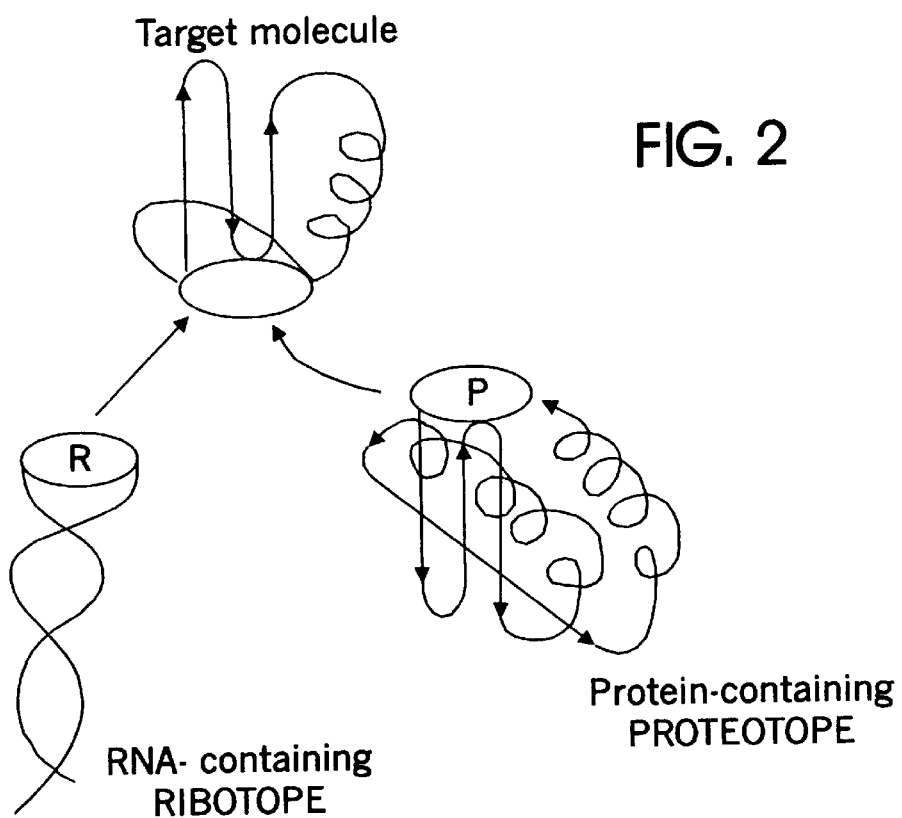
FIG. 2 is a schematic drawing illustrating that a ribotope and its corresponding proteotope compete for the same binding site on a target molecule.

The present invention is based on the finding that RNA molecules may function in vivo at sites where protein molecules otherwise interact (e.g., RNA and protein serve similar trans-acting roles). Accordingly, as used herein, such RNA conformations are referred to as "ribotopes" and the crossreacting conformational sequences on other molecules (typically proteins or peptides, but also other molecules as discussed below) as "proteotopes." The existence of such structural and/or functional mimetics indicates that regulatory events can be elicited via signals initiated by the binding or displacement of a proteotope by a ribotope, and vice versa. As used in the present invention, the ribotope and its mimetic proteotope are immunologically crossreactive and transact independently at a site on a cellular target molecule (as illustrated in FIG. 2), with the potential to elicit a regulatory signal. Although the ribotope and its mimetic proteotope may be structural mimics, the skilled artisan will be able to identify ribotope/proteotope mimetic pairs based upon functional mimicry, with functional mimicry being defined as the ability of each member of the ribotope/proteotope pair to competitively bind to a common cellular target. It will be appreciated that cellular targets in accordance with the present invention may be molecules (e.g., peptides and proteins) that are produced by or originate from any organism, including bacteria, viruses, fungi, protists, plants, and animals.

Figure 1:
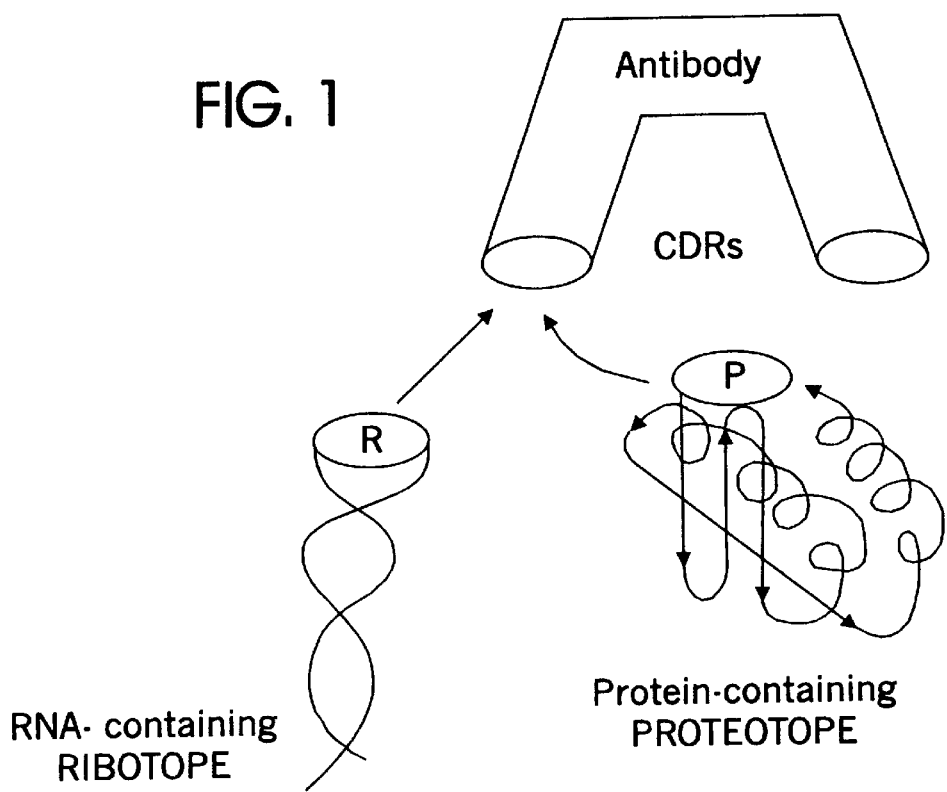
FIG. 1 is a schematic drawing illustrating the cross-reactivity between an RNA-containing ribotope, a protein-containing proteotope, and an antibody complementary determining region (CDR). The ribotope and its corresponding proteotope compete for the same binding site on the antibody.

While the methods described herein are, in general, directed to immunologically relevant aspects of the present invention, the skilled artisan will appreciate that the interaction between ribotopes and their functionally mimetic proteotopes has implications for all manner of protein-protein and protein-nucleic acid interaction within cells. In other words, while FIG. 1, for example, illustrates the present invention with respect to a ribotope and proteotope binding to an antibody, it is likely that only a very small subset of functional mimicry of the kind described herein would be detected by antibodies, whether they be autoantibodies or otherwise.

The term "epitope," as used herein, refers to a portion of a molecule which has a three-dimensional structure on an exposed surface to which an antigen binding protein can specifically bind, whether in the context of said molecule or as a portion thereof.

The term "ribotope," as used herein, refers to nucleic acid molecules or parts thereof that can function in vivo at sites where non-nucleic acid molecules (typically, proteins or peptides) otherwise interact, and which are conformationally similar to the cross-reacting non-nucleic acid molecule. Ribotopes may accordingly be single- or double-stranded DNA or RNA (e.g., mRNA, tRNA, rRNA, U1 snRNA, human Y RNA, etc.).

The term "proteotope," as used herein, refers to the non-nucleic acid (typically, a peptide or protein) molecule that is cross-reactive with the above-described ribotope at the same site on a target molecule (e.g., the specific binding site of a receptor). Cellular proteins containing proteotopes that crossreact with ribotopes, as defined in the present invention, are not restricted to any kind of protein, but may be primary autoantigens (i.e., proteins commonly observed to react with autoimmune sera), or secondary autoantigens (e.g., elongation factor 2 (EF-2)).

The skilled artisan will appreciate that autoantibodies may be useful in revealing ribotopes and proteotopes because they crossreact and the antibody mimics the target molecule to which the RNA and protein epitope bind in vivo.

The term "immunogen," as used herein, refers to a compound capable of eliciting an immune response, whether or not that compound is intentionally used to induce an immune response.

The term "antigen binding protein," as used herein, may refer to a protein or peptide that contains a binding site which is a functional mimic of a cellular target (e.g., a cell or viral protein) to which both a proteotope and a ribotope of the present invention can bind. Antigen binding proteins include, but are not limited to, the members of the immunoglobulin superfamily. Members of the immunoglobulin superfamily include, but are not limited to, major histocompatibility complex molecules, cell adhesion molecules (including both neuronal cell adhesion molecules and cellular cell adhesion molecules) virus receptors such as picornavirus receptors (e.g., poliovirus receptors, rhinovirus receptors), growth factor receptors (e.g., interleukin receptors, lymphokine receptors), other signaling molecules, T cell receptors (e.g., alpha-beta class and gamma-delta class T cell receptors), and antibodies. Antibodies and T cell receptors are currently preferred.

The term "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26, 403–11 (1989). Antibodies may be generated in vitro or in vivo whether natural or recombinant in origin. Additionally, antibodies may be autoantibodies produced by humans or animals, whether spontaneously generated or resulting from immunization or chemical induction.

Antibodies may be recombinant monoclonal antibodies produced according to the methods disclosed in U.S. Pat. No. 4,474,893 to Reading, or U.S. Pat. No. 4,816,567 to Cabilly et al. Antibodies may also be chemically constructed according to the method disclosed in Segel et al., U.S. Pat. No. 4,676,980. The term antibodies further includes fragments which retain the specific binding characteristics of the antibody from which they are derived, with such fragments including, for example, Fab, F(ab')$_2$, and Fc fragments, and the corresponding fragments obtained from antibodies other than IgG. Such fragments are produced by known techniques. For example, monoclonal Fab fragments may be produced in *Escherichia coli* by recombinant techniques known to those skilled in the art. See, e.g., W. Huse, *Science* 246, 1275–81 (1989).

The term "transcript" as used herein includes any transcript produced in any species of plant, animal, virus or protist, including the coding (sense) or noncoding (antisense) RNAs or DNAs. Accordingly, the term "transcript" may include transfer RNA, Y RNAs, 5S, 5.8S, 7S, 8S, large and small ribosomal RNAs, all intron RNAs, messenger RNAs, highly repetitive or highly iterative DNA sequences (e.g., LINES, SINES in mouse), Alu sequences and all other cellular, mitochondrial, episomal or plastid nucleic acids, and the precursor transcripts thereof.

Non-nucleic acid immunogens other than peptides which may be employed in the present invention include glycoproteins, fats, lipids, viruses (e.g., rhinovirus), polysaccharides, and carbohydrates. Peptides are preferred, with the term "peptide" as used herein referring to a peptide as a discrete molecule or residing in a protein.

As noted above, the present invention provides a method of generating a nucleic acid molecule which is immunologically cross-reactive with a non-nucleic acid immunogen by combining (i.e., under conditions which permit the specific binding of a nucleic acid species to an antibody CDR) an antibody which binds said immunogen with a pool of nucleic acid species obtained from a cell or virus that expresses the non-nucleic acid immunogen, and then recovering the nucleic acid species that is bound by the antibody.

Initially, suitable anti-peptide antibodies are obtained. For example, polyclonal antibodies used to carry out the present invention may be produced by immunizing a suitable animal (e.g., rabbit, goat, etc.) with a non-nucleic acid immunogen for which a nucleic acid epitope is desired, collecting immune serum from the animal, and removing the polyclonal antibodies from the immune serum, in accordance with known procedures. Monoclonal antibodies used to carry out the present invention may be produced in a hybridoma cell line according to the technique of Kohler and Milstein, *Nature* 265, 495–97 (1975).

As an alternative to antibodies, other members of the immunoglobulin superfamily such as T cell receptors may be employed, as noted above. T cell receptors are structurally and functionally analogous to antibodies, and can be manipulated in much the same way as antibodies. See generally A. Williams and A. Barclay, *Ann. Rev. Immunol.* 6, 381–405 (1988); S. Brostoff and M. Howell, *Clin. Immunol. & Immunopathol.* 62, 1–7 (1992).

Once suitable antibodies are obtained, they are then combined with a pool of nucleic acid species obtained from a cell or virus that expresses the non-nucleic acid immunogen that binds to the antibody. Suitable methods of obtaining such natural nucleic acid pools will be readily apparent to one skilled in the art. The nucleic acid pool may be formed of DNA molecules or RNA molecules, with pools of RNA molecules currently preferred, and mRNAs most preferred. In one embodiment of the invention, the nucleic acid pool comprises DNA, which DNA may be amplified by known methods prior to contacting the DNA with the antibody.

The nucleotide bases which form the pool may optionally be modified by, e.g., methylation, O-methylation, provision of base analogues with atypical hydrogen bonding patterns, etc. In general, natural pools of nucleic acids comprise a plurality of distinct nucleic acid species in an aqueous solution. Individual nucleic acid species within the pool may be 2, 3, 4, 5, or 6 nucleotides in length or more. There is no particular upper limit on the length of the nucleic acid species, with nucleic acids of 50, 100, or 200 or more nucleotides being suitable. The nucleic acid species may be linear or may possess some form of secondary structure, such as a stem and loop structure.

Combining the anti-peptide antibody with the nucleic acid pool may be facilitated by immobilizing the antibody on a solid support and contacting the nucleic acid pool (i.e., the aqueous solution carrying the pool) to the solid support, all in accordance with known techniques.

In one embodiment of the invention, the step of combining the nucleic acid pool with the antibody is followed by the step of separating nucleic acid species bound to said solid support (e.g., by washing away any unbound nucleic acid species, then eluting nucleic acid species bound to the solid support); then producing a pool of complementary nucleic acids from said nucleic acid species separated from said solid support (e.g., reverse transcribing a pool of cDNAs from a DNA or RNA pool); then amplifying the pool of complementary nucleic acids to produce a subset pool of nucleic acid species; and then repeating the step of combining the natural pool of nucleic acid species which binds with the antibody with the subset pool of nucleic acid species to produce a further subset pool of nucleic acids. This sequence of steps may be cyclically repeated to produce numerous subset pools, although a single cycle may in many cases be sufficient.

A separating step as described above preferably includes a wash step and an elution step. The wash step removes undesired nucleic acid species from the solid support, and the elution step removes the desired nucleic acid species from the solid support to provide the subset natural nucleic acid pool. The elution step may be carried out by any suitable means, such as phenol extraction. The separating step may be carried out at the same wash stringency at each cycle (i.e., as either a high stringency or low stringency wash), or the wash stringency may be changed between cycles (with stringency typically being adjusted from low stringency to high stringency as the cycles progress). See, e.g., E. Harlow and D. Lane, Antibodies, A Laboratory Manual (Cold Spring Harbor Laboratory 1988): R. Bentley and J. Keene, *Mol. Cell. Biol.* 11, 1829 (1991).

The amplifying step may be carried out in vivo or in vitro by any suitable means. See generally D. Kwoh and T. Kwoh, *Am. Biotechnol. Lab.* 8, 14–25 (1990). In vivo amplification may be carried out by standard recombinant DNA techniques, such as ligating cDNA produced as described above into a plasmid, and then taking that plasmid with inserts (or pool thereof) and transforming a bacterial culture therewith. See, e.g., J. Sambrook et al., *Molecular Cloning, A Laboratory Manual* (2d Ed. 1989) (Cold Spring Harbor Laboratory); J. Ma and M. Ptashne, *Cell* 51, 113–119 (1987); S. Deutscher and J. Keene, *Proc. Natl. Acad. Sci. USA* 85, 3299 (1988). Examples of suitable in vitro amplification techniques include, but are not limited to, polymerase chain reaction (see U.S. Pat. Nos. 4,683,202 and 4,683,195 to K. Mullis et al.), ligase chain reaction (see R. Weiss, *Science* 254, 1292 (1991)), strand displacement amplification (see G. Walker et al., *Proc. Natl. Acad. Sci. USA* 89, 392–396 (1992); G. Walker et al., *Nucleic Acids Res.* 20, 1691–1696 (1992)), transcription-based amplification (see D. Kwoh et al., *Proc. Natl. Acad Sci. USA* 86, 1173–1177 (1989)), self-sustained sequence replication (or "3SR") (see J. Guatelli et al., Proc. Natl. Acad. Sci. USA 87, 1874–1878 (1990)), the Qβ replicase system (see P. Lizardi et al., *BioTechnology* 6, 1197–1202 (1988)), nucleic acid sequence-based amplification (or "NASBA") (see R. Lewis, *Genetic Engineering News* 12 (9), 1 (1992)), the repair chain reaction (or "RCR") (see R. Lewis, supra), and boomerang DNA amplification (or "BDA")(see R. Lewis, supra).

Once a desired nucleic acid species is recovered, it may be amplified and/or sequenced and synthesized in accordance with known techniques as discussed above. A complementary nucleic acid (e.g., a cDNA) to the nucleic acid species may be produced by reverse transcription and the desired nucleic acid species produced in greater quantities by recombinant techniques. The immunological cross-reactivity of the recovered nucleic acid species with the non-nucleic acid immunogen it mimics may be confirmed by suitable immunoassay, such as blocking assays or competition experiments, carried out in accordance with known techniques.

The present invention provides a method of generating a nucleic acid molecule from a pathogen, which nucleic acid is immunologically cross-reactive with a non-nucleic acid immunogen expressed by that pathogen. The method is carried out in essentially the same manner as described above. Pathogenic organisms as used herein include viruses, bacteria, fungi and parasitic organisms.

In certain cases, transcripts of pathogens may be sufficiently abundant and stable to use direct transcription and immunoprecipitation of RNA epitopes, methods which are known to those skilled in the art. Examples of such viruses include negative stand RNA viruses such as vesicular stomatitis, rabies, (see e.g., M. G. Kurilla et al., *Journal of Virology* 50, 773–778 (1984)) and Ebola (see e.g., M. P. Kiley, et al., *Virology* 149, 251–254 (1986)). These viruses contain genomic RNAs, which may be radiolabeled in cell culture using any of several standard methods, and also express RNA in vitro using a virus encapsulated RNA polymerase. See H. Piwnica-Worms and J. D. Keene, *Virology* 125, 206–218 (1983). These sources of RNA can be used to identify ribotopes by fragmentation, partitioning and direct sequencing as described in S. D. Deutscher and J. D. Keene, *Proceedings of the National Academy of Sciences (USA)* 85, 3299–3303 (1988).

The present invention also provides a method of generating a non-nucleic acid immunogen which is immunologically cross-reactive with a nucleic acid by contacting (i.e., under conditions which permit the specific binding of an immunogen to an antibody CDR) an antibody which binds said nucleic acid with non-nucleic acid immunogens obtained from a cell or virus that expresses the nucleic acid, and then recovering an immunogen that is bound by the antibody.

Initially, suitable anti-nucleic acid antibodies are obtained. Antibodies may be obtained by the methods described above, wherein a nucleic acid is used as an antigen, in accordance with known techniques.

Once suitable antibodies are obtained, they are then contacted with a mixture of immunogens obtained from a cell or virus which expresses the nucleic acid that binds to the antibody. Suitable methods of obtaining such immunogens will be readily apparent to those skilled in the art. In one embodiment of the invention, an uninfected cell extract, an infected cell extract or an extract of an infectious agent such as a virus or bacterium is lysed using any standard method to provide the immunogens.

Contacting the anti-nucleic acid antibody with the immunogens may be facilitated by immobilizing the immunogens on a solid support, and then contacting the antibody to the solid support, all according to known techniques. In one embodiment of the invention, the immunogenic components of the cell or virus are first displayed on an SDS-acrylamide gel. The separated components are then transferred to an immobilized surface (e.g., nitrocellulose) and a standard antibody-immunogen complex-detecting technique (e.g., immunoblotting or Western blotting) is performed.

After the anti-nucleic acid antibody is contacted with the natural immunogens, the antibody-immunogen may be visualized by standard techniques known to those skilled in the art (e.g., radio-labelling or ELISA). The identified immunogens that bind to the anti-nucleic acid antibodies may then be separated from the antibody by a suitable method, as will be readily apparent to one skilled in the art.

Immunogens which are identified by reactivity with the anti-nucleic acid antibody may be purified by direct immunoprecipitation, by removal of the specific band from an acrylamide gel or (if the immunogen is a peptide or protein) by other standard methods of protein purification. The protein sequence may be determined directly using known methods.

The foregoing method further provides an isolated nucleic acid which inhibits complex formation between an antibody and a non-nucleic acid immunogen. Binding of the nucleic acid to such an antibody can be routinely determined in a standard competition assay in vitro, with nucleic acids of the invention having dissociation constants ($K_d$s) of $10^{-5}$, $10^{-7}$ or $10^{-8}$ up to $10^{-12}$ or $10^{-14}$ moles per liter. The format of competition assay is not critical, though enzyme-linked immunosorbent assay (ELISA) or radioimmunoassay (RIA) are particularly convenient. Nucleic acids of the invention have association constants ($K_a$s) which make them useful as inhibitors of the binding of non-nucleic acid immunogens to antibodies, with the $K_a$s for such nucleic acids ranging from $10^5$, $10^7$, $10^8$, or $10^9$ up to $10^{10}$ or $10^{12}$ liters per mole, with these values being determinable in the same manner as given above with respect to $K_d$s. The nucleic acid itself may mimic any of a broad variety of non-nucleic acid immunogens: for example, one embodiment of the foregoing is an isolated nucleic acid which inhibits complex formation between a self peptide autoantigen and an antibody, wherein said antibody is from a human or animal subject which expresses said self peptide. Such antibodies may be obtained from human subjects afflicted with an autoimmune disease, as noted above.

As with the nucleic acid species in the nucleic acid pool obtained from the immunogen-expressing cell or virus, isolated nucleic acids of the present invention may be of any length, typically of from 2, 3, 4, 5, or 6 nucleotides in length or more. Again, there is no particular upper limit on the length of the isolated nucleic acid, with nucleic acids of 50, 100, or 200 or more nucleotides being suitable. As above, the isolated nucleic acid may be linear or may possess some form of higher order structure, such as a stem and loop structure. Further, the isolated nucleic acid may be modified from that initially retrieved from the original pool, such as by removing primer segments or other portions thereof which are not critical for binding, or by making minor modifications to the structure of one or more of the individual nucleotides in the nucleic acid itself such as methylation, O-methylation, provision of nucleotide analogues with atypical patterns of hydrogen bonding, other modifications to prevent nucleophilic attack on the phosphodiester bond, and the like.

Nucleic acids and non-nucleic acid molecules cross-reactive therewith, as described above (hereinafter "active compounds") can be used in a variety of ways. For example, the active compounds may be conjugated, either directly or indirectly, and either covalently or non-covalently, to a molecule to be tagged thereby (i.e., a "tagged molecule"). The tagged molecule itself may be, for example, a protein or a heterologous nucleic acid. The tagged molecule can then be detected with antibodies known to bind the isolated active compound.

Active compounds of the invention may be used in methods of detecting an antibody which binds a predetermined immunogen. Such methods comprise contacting a biological sample suspected of containing the antibody to the active compound, which active compound is capable of inhibiting complex formation between the antibody and said immunogen, under conditions which permit the formation of a reaction product; and then detecting the presence or absence of the reaction product. Biological samples taken from human or animal subjects for use in this method are generally biological fluids such as serum, blood plasma, or ascites fluid. In the alternative, the sample taken from the subject can be a tissue sample (e.g., biopsy tissue; scrapings; etc.). Any suitable assay format can be used to carry out the detection of the reaction product, examples being radioimmunoassay, immunofluorescence methods, enzyme-linked immunoassays, and the like. Those skilled in the art will be familiar with numerous specific immunoassay formats and variations thereof which may be useful for carrying out the method disclosed herein. See generally E. Maggio, *Enzyme-Immunoassay*, (1980) (CRC Press, Inc., Boca Raton, Fla.).

Active compounds of the present invention may also be used to produce an immune response to an immunogen in a human or animal (e.g., dog, cat, horse, goat, rabbit) subject. In this case, the active compound serves as a surrogate immunogen for the second immunogen. The method comprises administering a active compound to the subject, which active compound is capable of inhibiting complex formation between an antibody and the immunogen, with the active compound being administered in an amount effective to induce an immune response in said animal to the immunogen. Techniques for enhancing the immunogenicity of the active compound which are known in the art may, if desired, be employed. Subjects may be administered active compounds of the present invention for this purpose to simply raise stocks of antibodies, or for therapeutic purposes to subjects in need of such treatment. Administration to a subject may be carried out by any suitable means, such as by subcutaneous injection, intravenous injection, intraperitoneal injection, and nasal spray. The amount of active compound administered will depend upon factors such as route of administration, the species of the subject, and the use of booster administrations.

Active compounds of the invention may be employed in methods of blocking complex formation between a second immunogen and an antigen-binding protein (typically an antibody) which binds the second immunogen. Such methods comprise contacting the antibody to an active compound, which active compound inhibits complex formation between the antibody and the second immunogen. The contacting step may be carried out in vitro (again typically by combining constituents in an aqueous solution), or may be carried out in vivo in a human or animal subject. Where carried out in vivo, the subject, dosage, route of administration, and other parameters may be as given above in connection with a method of inducing an immune response. Where carried out in vitro, again, numerous different formats for carrying out such blocking experiments will be known to those skilled in the art, as also discussed above.

Active compounds of the present invention may be prepared for administration to a subject as a pharmaceutical composition comprising the active compound in a pharmaceutically acceptable carrier. Preparation is typically carried out by intimately admixing the active compound with the carrier. The active compound is included in an amount sufficient to achieve the intended effect: i.e., induce an immune response or block complex formation between an antibody and an immunogen, as explained above. Pharmaceutically acceptable carriers may be solid or liquid carriers, such as sterile pyrogen-free phosphate-buffered saline solution. The carrier may optionally contain one or more adjuvants, such as aluminum hydroxide, aluminum phosphate, plant and animal oils, etc. In addition, the vaccine formulation may contain one or more stabilizers, with exemplary stabilizers including carbohydrates such as sorbitol, mannitol, starch, sucrose, dextran, and glucose; proteins such as albumin or casein; and buffers such as alkaline metal phosphates and the like.

The foregoing is explained in greater detail in the following non-limiting examples.

EXAMPLE 1

Identification of Ribotopes in Cellular RNAs

Polyadenylated messenger RNA extracted from any cell using standard methods are examined for the presence of ribotopes by preparing a cDNA library in any of several standard plasmid vectors which contain a transcription promoter site, such as the T7, T3 or SP6 RNA polymerase start site. These libraries are prepared as described in Gao, F., et al., *Proceedings of the National Academy of Sciences* (*USA*) 91, 11207–11211 (1994). These libraries contain flanking primer sites for amplification using the polymerase chain reaction (PCR). RNA transcripts are generated in vitro from this library, which can be prepared from a tissue or cell of interest. These transcripts represent essentially all of the messenger RNAs expressed in that tissue or cell, as well as antisense sequences which are complementary to the protein coding strand of the messenger RNA. The transcripts, whether sense or antisense, are partitioned using an antibody derived by immunization with proteotope-containing proteins present in the same tissue or cell; or by using an autoantibody derived from the same species as the library (i.e., human, mouse, etc.). Transcripts which bind to the antibody are eluted and converted to cDNA using reverse transcriptase and subsequently amplified by any of several known methods such as PCR. The purified RNA epitopes or ribotopes are identified by subsequent cloning and sequencing of the partitioned nucleic acids. The higher order structure of the RNA may be predicted using any of several known folding algorithms.

The method described here allows in vitro production of naturally-occurring RNAs, and a means to subsequently partition ribotopes from the total pool of messenger RNA sequences. However, it should be noted that it is not always necessary to use iterative in vitro amplification of ribotope sequences because antibody precipitation with subsequent washing of complexes which are bound to solid surfaces is usually sufficient to purify and identify the RNA species which bind to the antibody. Moreover, it is possible to introduce in vivo amplification methods such as plasmid growth in bacteria in order to obtain larger amounts of the desirable DNA expressing RNA epitope or ribotope.

It will further be apparent to the skilled artisan that although the use of naturally occurring RNA is described in the present example, any source of naturally occurring nucleic acids, including genomic DNA, cDNA and other nucleic acids, may be used in the practice of the present invention as described herein.

EXAMPLE 2

Identification of Ribotopes in Pathogen RNA Transcripts

Genomic RNA from the human immunodeficiency virus (HIV) is converted to cDNA using standard methods of reverse transcription-PCR and inserted into plasmid vectors which allow the production of in vitro transcripts. Both the sense and antisense transcripts derived from these pathogens are used to identify ribotopes as described above using antibodies prepared against proteotope-containing components of the host which the pathogen infects. Autoantibodies prepared from a compatible host are also be tested using ribotope-expressing cDNA libraries from these pathogenic organisms.

EXAMPLE 3

Identification of Proteotopes in Cells and Infectious Agents

Proteotopes are identified by immunoblotting experiments in which an uninfected cell extract, an infected cell extract or an extract of an infectious agent such as a virus or bacterium is lysed using any standard method and the components displayed on an SDS-acrylamide gel. The separated components can then be transferred to an immobilized surface such as nitrocellulose and standard immunoblotting or Western blotting performed. The transferred material can be probed using antibodies of choice which are first suspected of binding to a ribotope.

Crossreactive proteotopes bind to the same antibody which can be visualized on the blot using any number of methods such as radiolabel or ELISA. In one version of this method the antibody is affinity purified using the ribotope as substrate after it is immobilized on a solid surface. For example, the ribotope is bound to nitrocellulose as a matrix by heat treatment or crosslinking with ultraviolet light. Alternatively, the ribotope is tagged with biotin using standard methods and immobilized for affinity purification of specific antibodies by using avidin to bind the biotin. The antibody is bound and nonspecific antibodies washed away in phosphate buffered saline and the specific antibody eluted by treatment with buffer pH 3, or by digestion of the ribotope with ribonuclease.

Proteotopes which are identified by reactivity with the antibody are purified by direct immunoprecipitation, by removal of the specific band from an acrylamide gel or by other standard methods of protein purification. The protein sequence may be determined directly using known methods. Alternatively, the affinity purified antibody to the ribotope may be used directly to screen cDNA expression libraries which express the proteotope, thereby allowing identification of the protein containing the proteotope. The proteotope can be identified as a peptide subset to the protein using any number of methods to identify immunological epitopes on the surface of proteins. See e.g., M. R. Saitta, et al., *Journal of Immunology*, 152, 4192–4202 (1994), where many of these methods are described for proteins. These methods can be applied to any pathogen, as well as mammalian and other cells to identify and isolate the ribotope and proteotope pairs involved in structural and functional mimicry.

The foregoing examples are illustrative of the present invention, and are not to be construed as limiting thereof. The invention is defined by the following claims, with equivalents of the claims to be included therein.

That which is claimed is:

1. A method of making an immunogen that inhibits complex formation between an antigen binding protein and a nucleic acid, said method comprising the steps of:
    providing an antigen binding protein that specifically binds said nucleic acid;
    providing a mixture of immunogens obtained from a cell or virus that expresses said nucleic acid;
    contacting said mixture to said antigen binding protein so that said immunogen is bound thereto;
    separating said mixture from said antigen binding protein; and then
    separating said immunogen from said antigen binding protein.

2. A method according to claim 1, which antigen binding protein is immobilized on a solid support.

3. A method according to claim 1, which antigen binding protein is selected from the group consisting of IgG, IgM, IgA, and IgG immunoglobulins.

4. A method according to claim 1, which antigen binding protein is a T-cell receptor.

5. A method according to claim 1, which nucleic acid is an RNA.

6. A method according to claim 1, which nucleic acid is an mRNA.

7. A method according to claim 1, which nucleic acid is a DNA.

8. A method according to claim 1, which immunogen is selected from the group consisting of proteins and peptides.

9. A method according to claim 1, which mixture is a lysis product of said cell.

10. A method according to claim 1, which cell is a natural cell.

* * * * *